United States Patent [19]

Pletcher

[11] 4,077,126

[45] Mar. 7, 1978

[54] ORTHODONTIC BRACKET

[76] Inventor: Erwin C. Pletcher, P.O. Box 566, Rancho Santa Fe, Calif. 92067

[21] Appl. No.: 703,082

[22] Filed: Jul. 6, 1976

[51] Int. Cl.² .............................................. A61C 7/00
[52] U.S. Cl. ...................................................... 32/14 A
[58] Field of Search ............................. 32/14 A, 14 B

[56] References Cited

U.S. PATENT DOCUMENTS

| 2,011,575 | 8/1935 | Ford ..................................... 32/14 A |
| 3,444,621 | 5/1969 | Pletcher ............................... 32/14 A |
| 3,748,740 | 7/1973 | Wildman .............................. 32/14 A |

*Primary Examiner*—Robert Peshock
*Attorney, Agent, or Firm*—Christie, Parker & Hale

[57] ABSTRACT

An orthodontic bracket assembly having a locking member rotatably mounted within the body of a bracket member. The bracket body defines an arch-wire slot, and the locking member includes a hollow hub with a slotted portion which is rotatable into alignment with the arch-wire slot so an arch wire can be seated in both the body member and the hub. Rotation of the hub closes the arch-wire slot to lock the wire in place.

14 Claims, 10 Drawing Figures

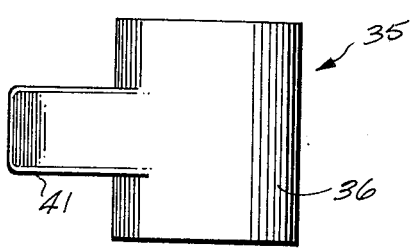
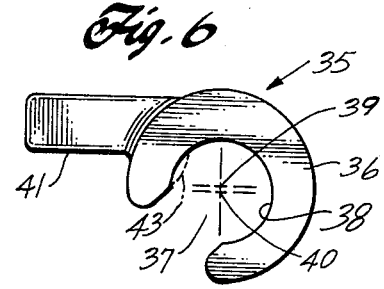
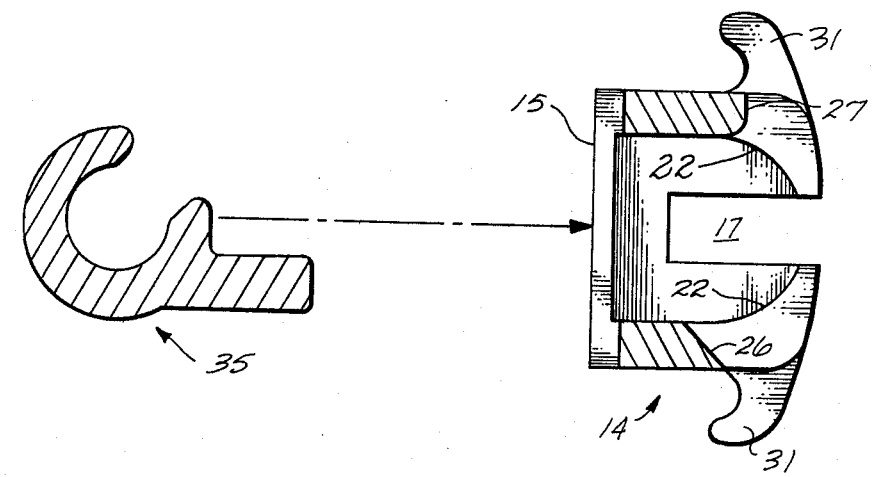
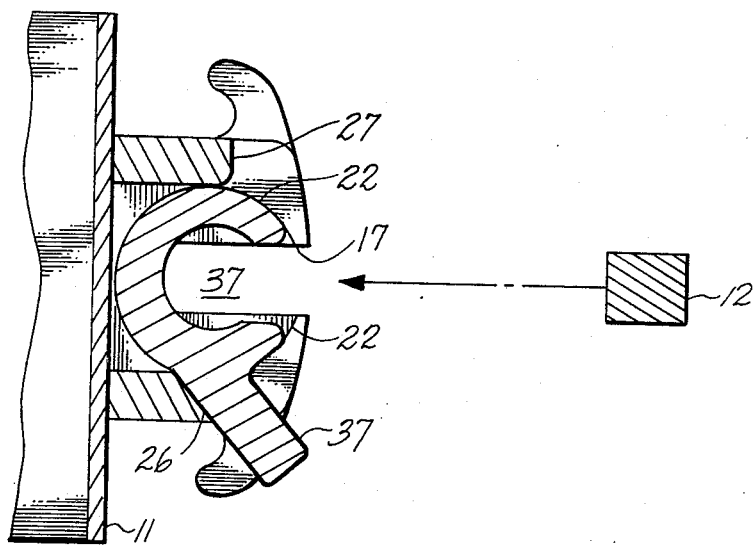

ORTHODONTIC BRACKET

BACKGROUND OF THE INVENTION

Orthodontic treatment of improperly positioned teeth involves the application of mechanical forces to urge the teeth into correct alignment and orientation. The most common form of treatment involves use of orthodontic brackets which are small slotted bodies configured for direct attachment to the front or labial surfaces of the teeth, or alternatively for attachment to bands which are in turn cemented or otherwise secured around the teeth. A resilient curved arch wire is then seated in the bracket slots, and the arch wire is bent or twisted before installation whereby the restoring force exerted by the seated resilient wire tends to shift the teeth into orthodontically correct alignment. Depending on the shape of the arch wire (both round and rectangular cross-sections are in common use) and the orientation of the bracket slot, it is possible to apply forces which will shift, rotate or tip the teeth in any desired direction.

Conventional orthodontic brackets include tie wings around which small ligature wires are tied to hold the arch wire in a securely seated position in the brackets. Ligatures or some other form of fastening means are essential to insure that the activated arch wire is properly positioned around the dental arch, and to prevent the wire from being dislodged from the bracket slots during chewing of food, brushing of the teeth, or application of other forces to the wire by the patient.

Orthodontists develop great skill in the manipulation of ligatures, but the installation of these small wires nevertheless requires considerable time during initial installation of an arch wire. It is also normally necessary to remove and replace the ligatures at one or more intermediate stage of orthodontic treatment involving sequential use of several different kinds of arch wires, leading to further essentially unproductive chair time for the orthodontist and possible discomfort for the patient. Ligatures also tend to make proper oral hygiene more difficult as the wires can trap food particles, and the twisted ends of a ligature may be shifted during chewing into a position where irritation of the patient's gums or cheek tissue occurs. Broken or dislodged ligatures may also require emergency patient visits to the orthodontist, and broken ligatures further present the hazard that a loose piece of wire may be swallowed or inhaled into the patient's breathing passages.

The bracket assembly of this invention eliminates the need for ligatures at most or all stages of treatment. A rotatable locking member is captively mounted in a bracket body, and is movable between open and closed positions to receive and lock an arch wire in a seated position. Simple rotation of the locking member enables rapid initial installation of an arch wire, and significantly facilitates exchange of arch wires during intermediate treatment phases. The locking member is easily manipulated by auxiliary personnel to minimize the time required for the orthodontist to insure proper installation or exchange of arch wires.

The bracket is smoothly contoured to minimize food-trapping recesses, and includes extensions or steps at each end of the arch-wire slot for improved application of force to teeth requiring rotation. The locking member is useful in both light-wire and edgewise techniques without restriction on arch-wire cross-section, and does not restrict orientation of the arch-wire slot to enable application of torquing or other force vectors. Tie wings may be provided on the bracket to enable ligation of an arch wire which cannot be fully seated in the bracket during early treatment of a severely malpositioned tooth or in any case where complete bracket engagement is difficult or unattainable.

SUMMARY OF THE INVENTION

This invention relates to an orthodontic bracket assembly which includes a bracket member having a base, and a body portion extending from the base to define a mesiodistally extended arch-wire slot. The body portion of the bracket member is hollow, and the interior surfaces of the body portion define an arcuate inwardly facing seat surface adjacent and extending on opposite sides of the arch-wire slot.

The bracket assembly further includes a locking member rotatably positioned within the bracket body portion against the arcuate seat surface. The locking member defines a slot which is alignable with the bracket-body arch-wire slot so an arch wire can be received in both slots. The locking member is rotatable within the bracket body portion to move the slots out of alignment and thereby lock the arch wire to the bracket member.

Preferably, the locking member includes a generally cylindrical hollow hub, and the locking-member arch-wire slot is formed through the hub wall. The locking member further includes a handle extending from the hub, and a longitudinal axis of the handle is preferably radially off-set from a central axis of an outer cylindrical surface of the hub. In one form, the hub has inner and outer surfaces which are surfaces of revolution formed about different central axes whereby the hub increases in cross-sectional thickness as it extends away from the slot.

A detent may be provided in the bracket-member body portion to hold the locking member in a closed position, or a detent-like rib may be formed on the inner surface of the hub to provide a detent action as the hub is rotated about the arch wire. Preferably, the body portion includes a forwardly opening and generally vertically oriented slot extending above and below the arch-wire slot to receive the locking-member handle in the open and closed position. The bracket base preferably includes steps or forwardly extending portions at opposite ends of the body-portion arch-wire slot to lengthen the floor surface of the arch-wire slot.

DESCRIPTION OF THE DRAWINGS

FIG. 5 is a front view of the locking member;

FIG. 6 is an end view of the locking member;

FIG. 7 is a pre-assembly view of the locking member and the sectioned bracket member as viewed on line 7—7 of FIG. 2;

FIG. 8 is a view similar to FIG. 7 except showing the parts in an assembled condition and ready to receive an arch wire;

DESCRIPTION OF THE PREFERRED EMBODIMENTS

Figure 1:
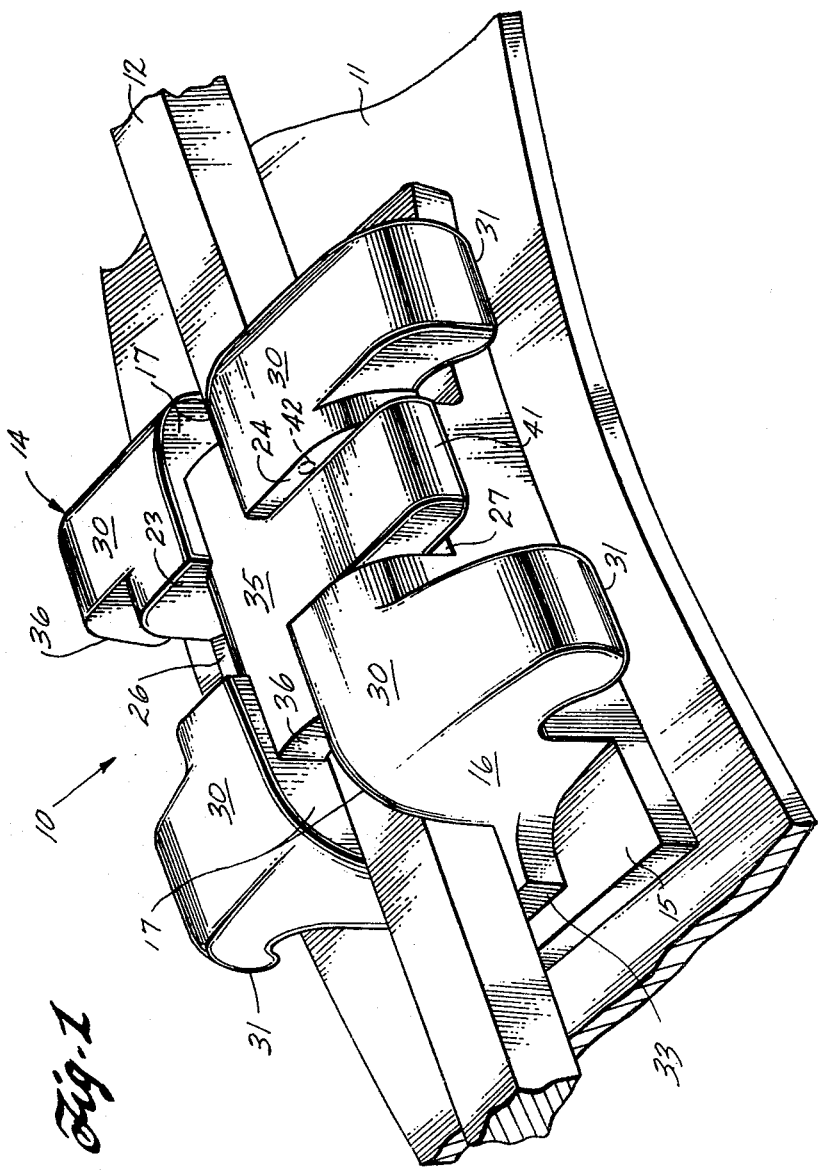
FIG. 1 is a perspective view of an orthodontic bracket assembly according to the invention, the assembly being mounted on a tooth band and shown locked around an arch wire.

An orthodontic bracket assembly 10 according to the invention is shown in FIG. 1 as welded or otherwise secured to a conventional metal tooth band 11 (only a portion of which is illustrated) configured for cemented attachment to a tooth. A conventional edgewise arch wire 12 is seated in the bracket to deliver corrective force to a tooth (not shown) on which the band and bracket assembly are mounted.

Bracket assembly 10 includes a bracket member 14 (best seen in FIGS. 2–4 and 7) with a base 15 which is preferably slightly concave to accommodate the normal curvature of the tooth band and tooth. A body portion 16 extends forwardly from the base of the bracket, and the body portion defines a forwardly open mesiodistally extending slot 17 to receive an arch wire. The slot is normally rectangular in cross-section as seen in FIG. 7 to be useful with arch wires of either round or rectangular cross-section.

The interior of the bracket body is hollow, and a rectangular window-like opening 20 extends from the rear surface of the bracket base into communication with the arch-wire slot. The front or labial walls of the bracket body above and below the arch-wire slot extend over the hollow interior to define a semi-cylindrical socket formed by a plurality of curved and inwardly or lingually facing seat surfaces 22.

A pair of openings 23 and 24 are formed in the central part of the bracket body to define a forwardly opening and generally vertically (occlusal-opical) oriented handle-receiving slot which is perpendicular to arch-wire slot 17. Preferably, the bases of these slot-defining openings are shaped to define a beveled or forwardly sloping stop surface 26 and a vertical stop surface 27 on opposite sides of the arch-wire slot as best seen in FIG. 7.

Bracket member 14 is thus in effect comprised of base 15 and four post-like projections 30 which are separated by the locking-member socket and the vertically and horizontally oriented slots. Preferably, rearwardly extending tie wings 31 are formed on projections 30 to enable use of a ligature wire (not shown) at any time it is not possible to achieve normal seating of the arch wire. This may be particularly advisable during initial treatment stages of grossly malpositioned teeth. In this form, the bracket has substantially the appearance of a Siamese or twin-wing bracket except for the provision of the hollow interior which defines the locking-member socket and opening 20 which extends rearwardly from the socket to the rear face of the bracket base.

In a preferred form, forwardly extending steps 33 are integrally formed with base 15 at opposite ends of arch-wire slot 17. These steps effectively increase the mesiodistal length of the base or floor of the arch-wire slot, providing increased leverage when the bracket assembly is used to deliver rotational force to a tooth.

A locking member 35 for the bracket assembly is shown in FIGS. 5 and 6. The locking member includes a cylindrical tube or hub 36 with a radially extending arch-wire-receiving slot 37 extending through one wall of the hub. The interior of hub 36 defines a cylindrical bore 38 and the outer edges of slot 37 are rounded or chamfered to avoid interference with the arch wire during hub rotation or installation of the arch wire.

Although the inner and outer cylindrical surfaces of hub 36 are both surfaces of revolution, they are formed around different central axes whereby the cross-sectional thickness of the hub is smallest at the hub-wall ends adjacent the slot. In other words, central axis 39 of the outer surface is positioned slightly above central axis 40 of the inner surface as viewed in FIG. 6 to produce a hub-wall cross-section which tapers slightly from a central part of the wall toward the wall ends adjacent the hub arch-wire slot. In a typical configuration, the outside diameter of the hub is about 0.060 inch, the inside diameter of the hub is about 0.036 inch, and the central axes of these surfaces are vertically spaced apart (as viewed in FIG. 6) by about 0.002 inch.

A tab or handle 41 extends from and is integrally formed with the hub. As best seen in FIG. 6, the longitudinal axis of the handle is radially offset from the central axis of the hub so the handle extends more nearly tangentially than radially from the hub. The offset handle is more readily accessible to the orthodontist when the locking member is to be rotated, and also strengthens the locking member as well as the bracket body (because the depth of the handle-receiving slots is minimized).

In a presently preferred form, bracket member 14 and locking member 35 are cast parts made from a suitable dental alloy which can be welded to a stainless-steel tooth band. Casting is preferred for forming the interior contours of the bracket on a production basis. The bracket assembly is not restricted to metallic construction, and is suitable for injection molding from plastic materials which can be directly cemented to teeth, or alternatively to a tooth band. A composite construction is also feasible, with the locking member, for example, being made of metal, and the bracket member being molded plastic.

The bracket and locking members are shown in FIG. 7 positioned for preliminary assembly with the locking member disposed behind base 15 in alignment with opening 20 through the base. The length and width of opening 20 are dimensioned to be slightly larger than the corresponding dimensions of the locking member, whereby the locking member can be inserted through the rear of the bracket to seat against surfaces 22.

With the parts in this position, base 15 is then welded or otherwise secured to tooth band 11. This step closes window-like opening 20 in the rear surface of the bracket member, and makes the locking member captive within the bracket member. If the bracket is intended for direct cementation to a tooth, a thin sheet-metal plate (not shown) is secured over opening 20 to prevent ingress of cement into the interior of the bracket body.

After the bracket assembly is positioned on a tooth, handle 41 is positioned against sloping stop surface 26 to align slots 17 and 37 as shown in FIG. 8. The sloping stop surface places the handle in a readily accessible position when the locking member is in this open position. Arch wire 12 is then moved into the aligned slots to be fully seated in the bracket body and locking-member hub. The locking member is next rotated by moving handle 41 against vertical stop surface 27 to move slots 17 and 37 out of alignment and make the arch wire captive in the bracket body as shown in FIG. 9.

Figure 9:
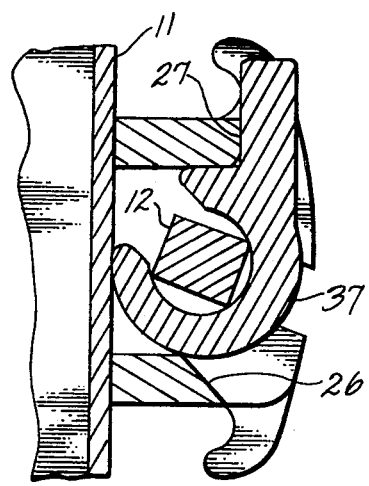
FIG. 9 is a view similar to FIG. 7 except showing the parts fully assembled and the arch wire locked in a torqued arch-wire slot.

It is not essential that arch-wire slot 17 be perpendicularly oriented to base 15, and a torqued slot configuration is shown in FIG. 9. In effect, slot 17 is simply rotated around the axis of the seated arch wire to achieve the desired degree of torque angulation.

Figure 2:
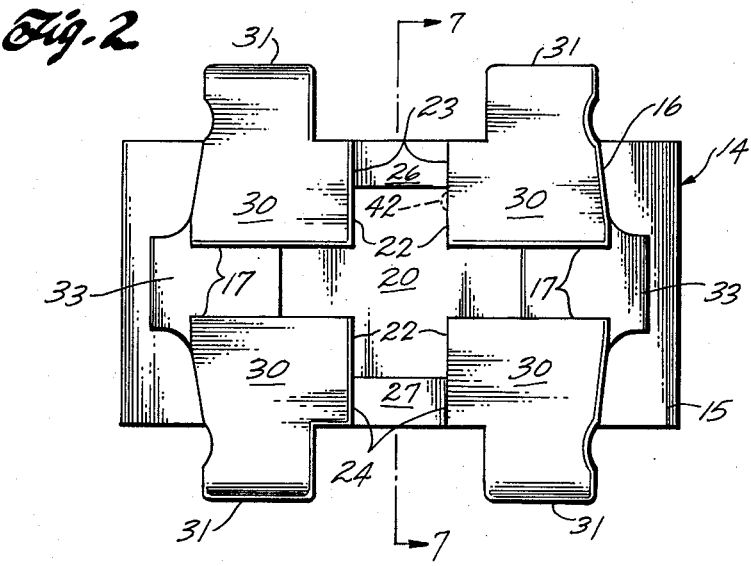
FIG. 2 is a front view of a bracket member used in the assembly.
Figure 3:
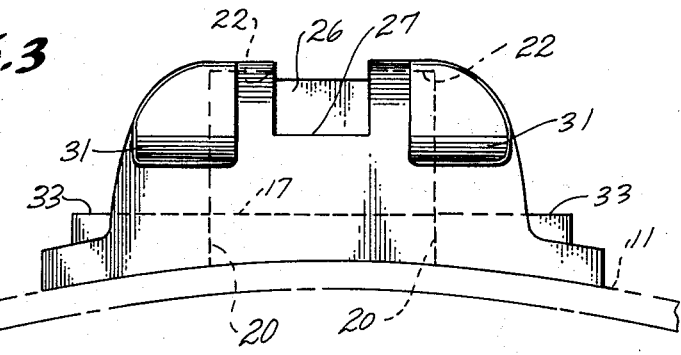
FIG. 3 is a bottom view of the bracket member.
Figure 4:
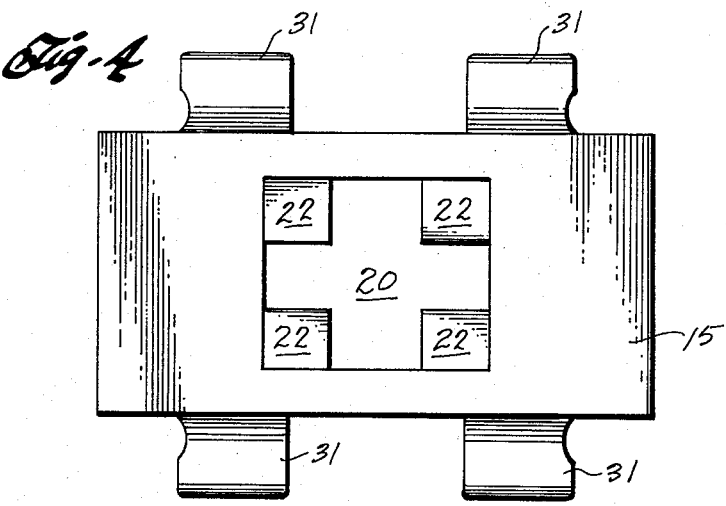
FIG. 4 is a rear view of the bracket member.

If desired, small detent buttons or projections 42 shown in phantom line in FIGS. 1 and 2 can be molded adjacent one or both labial edges of the bracket-body surfaces forming the sides of opening 24 in order to increase resistance to movement of the locking member out of the locked position shown in FIG. 9. Alternatively, a mesiodistally extending rib 43 (shown in phantom line in FIG. 6) can be molded in the inner surface of hub 36 to ride over an edge of the edge-wise arch wire just before handle 41 abuts stop surface 27. In practice, it has been found that detent-like stops of this type are normally unnecessary because the friction of the activated arch wire is sufficient to hold the hub in a locked position.

A further force tending to prevent unwanted rotation of the locking-member hub out of a locked position is provided by a slight wedging action during final rotation of handle 41 against stop surface 27. This action arises from the non-concentric axes of the inner and outer cylindrical surfaces of hub 36 as explained above. The arch wire is free, however, to move mesiodistally or axially with respect to the bracket assembly as is desirable in certain modes of treatment such as mesiodistal space closure or tooth rotation. Arch-wire removal is achieved simply by rotating the locking member to the open position and lifting the arch wire out of the aligned slots.

Figure 10:
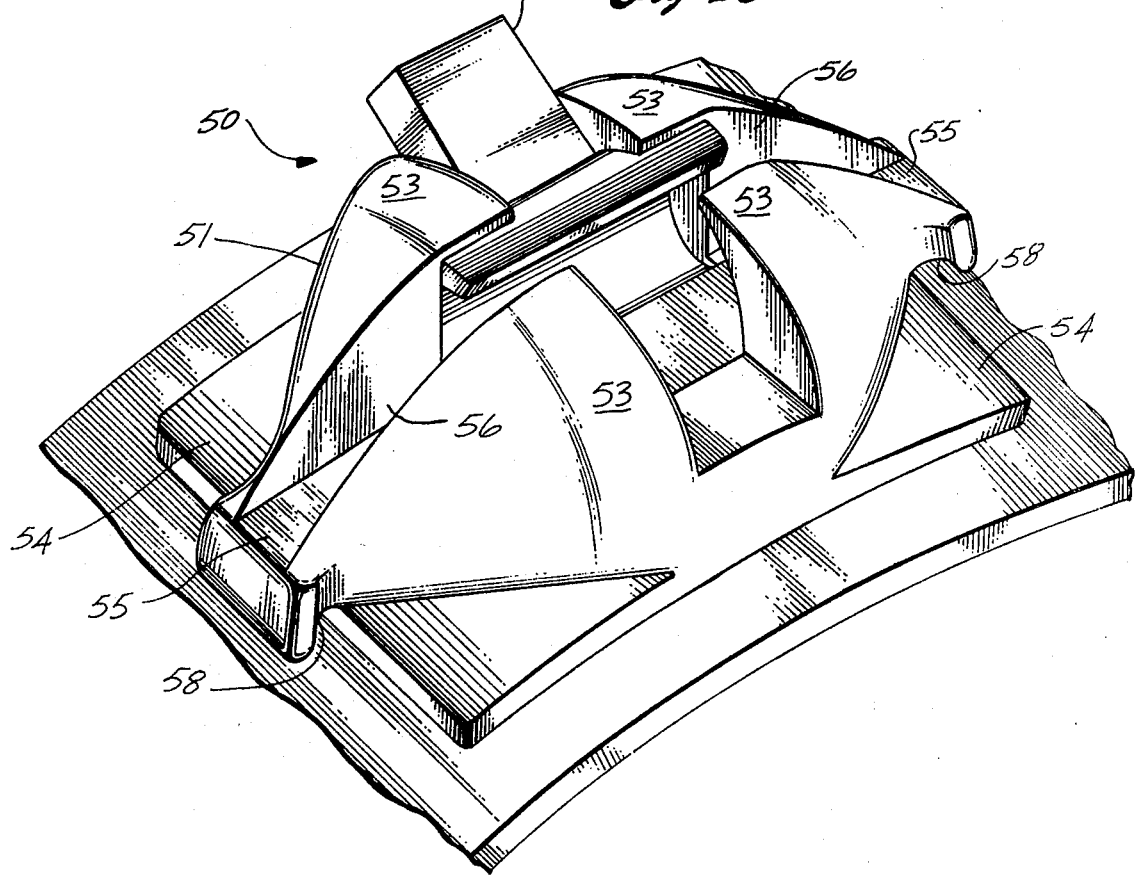
FIG. 10 is a perspective view of an alternative embodiment of the bracket assembly.

An alternative embodiment of the invention is shown in FIG. 10 which illustrates a bracket assembly 50 with a bracket member 51 and a locking member 52 (shown as rotated slightly away from a fully open position for clarity of illustration). The locking member and internal construction of the bracket-member body are identical to the embodiment already described. Normal tie wings are omitted, however, and the front surfaces of post-like projections 53 of the bracket body slope smoothly in a lingual direction to join an integral bracket base 54. The result is a very clean bracket which has little tendency to trap food particles, or to irritate cheek tissue of the patient.

As in bracket member 14, forwardly or labially extended steps 55 are integrally formed with base 54 at opposite ends of an arch-wire slot 56 to increase bracket leverage during rotational treatment. Preferably, the ends of steps 55 are lingually or rearwardly extended to form a pair of ligature-wire seats or notches 58 in the undersurface of the steps. Normal use of the bracket will often not require any auxiliary ligatures, but notches 58 provide ligature capability if, for example, the arch wire is to be anchored against axial (mesiodistal) movement with respect to the bracket.

Bracket assemblies 10 and 50 both have the advantage that the orthodontist need not learn any new manipulative techniques, and auxiliary ligatures or elastics may be used in a conventional manner if desired at any stage of treatment. The bracket assemblies are well suited for rotation or torquing movements of teeth without requiring auxiliary attachments. In cases where the arch wire cannot be fully seated, the locking member can be rotated to a closed position, and a ligature threaded through the locking-member hub to provide ligature anchorage.

There has been described an orthodontic bracket which is quick and simple for the orthodontist to use, and comfortable for the patient as well as providing improved physiological cleanliness in the mouth. The new bracket will in many cases eliminate time-consuming ligation procedures, but is nevertheless sufficiently flexible to accommodate ligatures in treatment situations requiring auxiliary anchoring of an arch wire.

What is claimed is:

1. An orthodontic bracket assembly comprising:
    a bracket member having a base, and having a body portion extending from the base and defining a slot to receive an elongated arch wire, the body portion being hollow to define an arcuate inwardly facing seat surface adjacent the bracket-body slot; and
    a hollow locking member rotatably positioned within the bracket body portion against the seat surface, the locking member defining a slot which is alignable with the bracket-body slot so the arch wire can be received in both slots and the locking member can then be rotated about a longitudinal axis of the arch wire to misalign the slots and make the arch wire captive within the lock member, thereby locking the arch wire to the bracket member.

2. The assembly defined in claim 1 wherein the locking member includes a generally cylindrical hollow hub, the locking-member slot being formed through a wall of the hub, and wherein the bracket-body slot is rectangular in cross section.

3. The assembly defined in claim 2 wherein the locking member includes a handle extending from the hub.

4. The assembly defined in claim 3 wherein the locking-member handle is elongated, and a longitudinal axis of the handle is radially offset from a generally central axis of an outer cylindrical surface of the hub.

5. The assembly defined in claim 2 wherein the hub has inner and outer surfaces which are surfaces of revolution formed about different central axes whereby the hub has a varying cross-sectional thickness.

6. The assembly defined in claim 2 wherein the hub has an inner surface which defines a radially inwardly extending rib forming a detent tending to hold the locking member in a closed position when an arch wire is seated in the hub.

7. The assembly defined in claim 3 wherein the bracket-member body portion defines a forwardly opening second slot oriented generally perpendicularly to the arch-wire slot, the locking-member handle being receivable in the second slot.

8. The assembly defined in claim 7 wherein the second slot extends above and below the arch-wire slot to define a pair of stop surfaces for the handle.

9. The assembly defined in claim 8 wherein one of the stop surfaces is generally parallel to the bracket base, and the other stop surface slopes away from the bracket base.

10. The assembly defined in claim 1 wherein the bracket base includes forwardly extending portions at opposite ends of the arch-wire slot to lengthen a floor surface of the arch-wire slot.

11. The assembly defined in claim 1 wherein the bracket member and locking member are cast metal components.

12. The assembly defined in claim 1 wherein the bracket-member base has an opening therethrough in communication with the hollow interior of the body portion, the locking member being configured for insertion through the base opening into the interior of the body portion.

13. The assembly defined in claim 1 wherein the body portion includes tie wings extending above and below the bracket-body arch-wire slot and rearwardly toward the base to enable anchorage of a ligature.

14. The assembly defined in claim 1 wherein integrally formed, distally extending steps are disposed at opposite ends of the bracket-body arch-wire slot to lengthen a floor surface of the slot, and the steps have a notched lingual surface extending beyond the base to enable anchorage of a ligature.

* * * * *